United States Patent
Higashi et al.

(10) Patent No.: US 12,091,382 B2
(45) Date of Patent: Sep. 17, 2024

(54) METHOD FOR PRODUCING FLUORINATED IODINATED ORGANIC COMPOUND

(71) Applicants: DAIKIN INDUSTRIES, LTD., Osaka (JP); SAGA UNIVERSITY, Saga (JP)

(72) Inventors: Masahiro Higashi, Osaka (JP); Yosuke Kishikawa, Osaka (JP); Tsugio Kitamura, Saga (JP)

(73) Assignees: DAIKIN INDUSTRIES, LTD., Osaka (JP); SAGA UNIVERSITY, Saga (JP)

( * ) Notice: Subject to any disclaimer, the term of this patent is extended or adjusted under 35 U.S.C. 154(b) by 0 days.

(21) Appl. No.: 17/522,312

(22) Filed: Nov. 9, 2021

(65) Prior Publication Data

US 2022/0064098 A1    Mar. 3, 2022

Related U.S. Application Data

(63) Continuation of application No. PCT/JP2020/018688, filed on May 8, 2020.

(30) Foreign Application Priority Data

May 10, 2019 (JP) .................. 2019-090051
Aug. 22, 2019 (JP) .................. 2019-152109

(51) Int. Cl.
  *C07C 17/08* (2006.01)
  *C07C 29/62* (2006.01)
  *C07C 67/307* (2006.01)

(52) U.S. Cl.
  CPC ............ *C07C 67/307* (2013.01); *C07C 17/08* (2013.01); *C07C 29/62* (2013.01)

(58) Field of Classification Search
  CPC ........ C07C 17/08; C07C 29/62; C07C 67/307
  See application file for complete search history.

(56) References Cited

U.S. PATENT DOCUMENTS

| | | | |
|---|---|---|---|
| 3,140,320 A | | 7/1964 | Weinmayr |
| 3,830,857 A | * | 8/1974 | Millauer .................. C07C 17/04 570/174 |
| 4,051,168 A | * | 9/1977 | Feiring .................... C07C 17/14 562/492 |
| 5,481,028 A | * | 1/1996 | Petrov .................... C07C 303/22 570/166 |
| 5,866,731 A | * | 2/1999 | Watanabe ............. C07C 17/087 570/248 |
| 6,946,582 B2 | * | 9/2005 | Katsube .................. C07C 67/11 570/174 |
| 7,718,568 B2 | | 5/2010 | Gaffney et al. |

FOREIGN PATENT DOCUMENTS

| | | |
|---|---|---|
| AU | 2003217726 | 10/2003 |
| JP | 52-68109 | 6/1977 |
| JP | 2002-363110 | 12/2002 |
| JP | 2002-363111 | 12/2002 |
| JP | 2009-515876 | 4/2009 |
| KR | 10-0569245 | 4/2006 |
| WO | 2007/056148 | 5/2007 |
| WO | 2007/079431 | 7/2007 |
| WO | 2017/186567 | 11/2017 |

OTHER PUBLICATIONS

Banik, S.M., et al., Catalytic, asymmetric difluorination of alkenes to generate difluoromethylated stereocenters, Science, vol. 353, issue 6294, pp. 51-54 (Year: 2016).*

Linclua, B., 3,3,4,4-tetrafluoro-4-bromo-1-butene and 3,3,4,4-tetrafluoro-4-ido-1-butene, University of Southampton, Southampton, UK, e-EROS Encyclopedia of Reagents for Organic Synthesis, 1-2, John Wiley & Sons, Ltd., 2 pages (Year: 2007).*

Ukigai, H,. et al., Stereoselective synthesis of idofluoroalkenes by idofluorination of alkynes using IF5-pyridine-HF, Tetrahedron Letters, 57(12), pp. 1379-1381 (Year: 2016).*

Ishida, S., et al., Site selectivities in fluorination, Graduate School of Sciences and Technology for Innovation, Yamaguchi University, 2018, 17 pages (Year: 2018).*

International Search Report issued Jul. 21, 2020 in International (PCT) Application No. PCT/JP2020/018688.

V.G. Dryuk et al., Kurs Organicheskoy Khimii (A Course in Organic Chemistry), K.: Vishcha shk. Golovnoe izd-vo, 1987. 400 p, with English language translation.

Yu. D. Tretyakov et al., Neorganicheskaya khimiya (Inorganic Chemistry). vol. 1. Publishing house of Moscow University. Moscow: 2007, with English language translation.

Yu. D. Tretyakov et al., Neorganicheskaya khimiya (Inorganic Chemistry). vol. 2. Publishing house of Moscow University. Moscow: 2007, with English language translation.

(Continued)

*Primary Examiner* — Yate' K Cutliff
(74) *Attorney, Agent, or Firm* — Wenderoth, Lind & Ponack, L.L.P.

(57) ABSTRACT

The present disclosure addresses the problem of providing a novel method for producing a fluorinated iodinated organic compound.

The problem can be solved by a method for producing a fluorinated iodinated organic compound, comprising reacting a compound represented by formula (1):

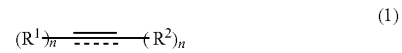

(1)

wherein $R^1$ and $R^2$ are each independently a hydrogen atom, a halogen atom, or an organic group, or $R^1$ and $R^2$ optionally form a ring together with the two adjacent carbon atoms; and n is 1 or 2, with a fluorine source, an iodine source, and an oxidizing agent or radical generator to add fluorine and iodine to the double bond or triple bond.

16 Claims, No Drawings

(56) References Cited

OTHER PUBLICATIONS

Jiaxing Huang et al., "Thermal decomposition analysis of 2,2-di-(tert-butylperoxy) butane in non-isothermal condition by DSC and GC/MS", Thermochimica Acta, 2018.

E.T. Oganesyan, Rukovodstvo po khimii postupayushchim v vuzy: Sprav. posobie (A Guide in Chemistry for Prospective Students: A Reference Book)—M.: Vyssh. Sh., 1987.—399 p, with English language translation.

English language translation of International Preliminary Report on Patentability issued Nov. 16, 2021 in corresponding International (PCT) Patent Application No. PCT/JP2020/018688.

Andrienko, O. S. et al., "Practical techniques for introducing fluorine into organic compounds", Publishing House for Scientific and Technical Literature, 2010, 176 c., pp. 43 and 166, with English translation.

Yu. S. Shabarov, "Organic Chemistry", 2011, 848 c., p. 385, with English translation.

Reutov, O. A. et al., "Organic Chemistry in 4 Parts", Part 1: Textbook for chemistry students, 2004, 567 c., p. 387, with English translation.

Extended European Search Report issued May 8, 2023 in corresponding European Patent Application No. 20805493.2, pp. 1-9.

* cited by examiner

METHOD FOR PRODUCING FLUORINATED IODINATED ORGANIC COMPOUND

TECHNICAL FIELD

The present disclosure relates to a method for producing a fluorinated iodinated organic compound.

BACKGROUND ART

Fluorinated iodinated organic compounds are extremely important compounds as various chemical products, such as functional materials, pharmaceutical and agrochemical compounds, and electronic materials; as well as intermediates thereof.

As a method for producing a fluorinated iodinated organic compound, for example, Patent Literature (PTL) 1 proposes a method for adding fluorine and iodine to a carbon-carbon double bond of an organic compound in the presence of $IF_5$, iodine, and an organic base under more strongly acidic conditions.

CITATION LIST

Patent Literature

PTL 1: JP2002-363110A

SUMMARY

The present disclosure includes the following embodiments.

Item 1.

A method for producing a fluorine and iodine adduct of a compound represented by formula (1):

  (1)

wherein
R$^1$ and R$^2$ are each independently a hydrogen atom, a halogen atom, or an organic group, or R$^1$ and R$^2$ optionally form a ring together with the two adjacent carbon atoms;
n is 1 or 2; and
the symbol

is a double bond or a triple bond, with the proviso that
when the symbol is a triple bond, n is 1,
when the symbol is a double bond, n is 2,
two R$^1$s are optionally the same or different,
two R$^2$s are optionally the same or different, or
two R$^1$s or two R$^2$s optionally form a ring together with their adjacent carbon atom,
the method comprising reacting the compound represented by formula (1) with
(A) at least one fluorine source selected from the group consisting of hydrogen fluoride, hydrogen fluoride salts, and fluoride salts,
(B) at least one iodine source selected from the group consisting of iodine and iodide salts, and
(C) at least one compound selected from the group consisting of oxidizing agents and radical generators, to add fluorine and iodine to the double bond or triple bond.

Advantageous Effects

According to the present disclosure, a novel method for producing a fluorinated iodinated organic compound is provided.

DESCRIPTION OF EMBODIMENTS

The above overview of the present disclosure is not intended to describe each of the disclosed embodiments or all of the implementations of the present disclosure.

The following description of the present disclosure more specifically exemplifies the embodiments of the examples.

Guidance is provided through examples in several parts of the present disclosure, and these examples can be used in various combinations.

In each case, the group of examples can function as a non-exclusive and representative group.

All publications, patents, and patent applications cited herein are incorporated herein by reference in their entirety.

Terms

Unless otherwise specified, the symbols and abbreviations in the present specification can be understood in the context of the present specification in the meanings commonly used in the technical field to which the present disclosure belongs.

In the present specification, the terms "comprise" and "contain" are used with the intention of including the terms "consisting essentially of" and "consisting of."

Unless otherwise specified, the steps, treatments, or operations described in the present specification may be performed at room temperature.

In the present specification, room temperature can refer to a temperature within the range of 10 to 40° C.

In the present specification, the phrase "$C_{n-m}$" (n and m are each a number) indicates that the number of carbon atoms is n or more and m or less, as can be generally understood by a person skilled in the art.

In the present specification, the phrase "compound represented by formula (N)" (N is a number) can be referred to as "compound (N)."

In the present specification, unless otherwise specified, examples of the "halogen atom" may include fluorine, chlorine, bromine, and iodine.

In the present specification, the "organic group" refers to a group containing one or more carbon atoms.

Examples of the "organic group" may include:
an alkyl group optionally having one or more substituents,
an alkenyl group optionally having one or more substituents,
an alkynyl group optionally having one or more substituents,
a cycloalkyl group optionally having one or more substituents,
a cycloalkenyl group optionally having one or more substituents,
a cycloalkadienyl group optionally having one or more substituents,
an aryl group optionally having one or more substituents,
an aralkyl group optionally having one or more substituents, a non-aromatic heterocyclic group optionally having one or more substituents, a heteroaryl group optionally having one or more substituents, a cyano group, an aldehyde group, a carboxyl group,

R'O—,

R'CO—,

R'COO—,

R'SO$_2$—,

R'OCO—, and

R'OSO$_2$—

(in these formulas, R' is independently an alkyl group optionally having one or more substituents, an alkenyl group optionally having one or more substituents, an alkynyl group optionally having one or more substituents, a cycloalkyl group optionally having one or more substituents, a cycloalkenyl group optionally having one or more substituents, a cycloalkadienyl group optionally having one or more substituents, an aryl group optionally having one or more substituents, an aralkyl group optionally having one or more substituents, a non-aromatic heterocyclic group optionally having one or more substituents, or a heteroaryl group optionally having one or more substituents).

In the present specification, unless otherwise specified, examples of the "hydrocarbon group" may include an alkyl group, an alkenyl group, an alkynyl group, a cycloalkyl group, a cycloalkenyl group, a cycloalkadienyl group, an aryl group, an aralkyl group, and a group that is a combination of these groups.

In the present specification, unless otherwise specified, examples of the "alkyl group" may include linear or branched $C_1$-$C_{16}$ alkyl groups (e.g., $C_1$-$C_{14}$ alkyl groups and $C_1$-$C_{12}$ alkyl groups), such as methyl, ethyl, propyl, isopropyl, butyl, isobutyl, sec-butyl, tert-butyl, pentyl, isopentyl, neopentyl, hexyl, heptyl, octyl, nonyl, and decyl.

In the present specification, unless otherwise specified, examples of the "alkenyl group" may include linear or branched $C_2$-$C_{10}$ alkenyl groups, such as vinyl, 1-propen-1-yl, 2-propen-1-yl, isopropenyl, 2-buten-1-yl, 4-penten-1-yl, and 5-hexen-1-yl.

In the present specification, unless otherwise specified, examples of the "alkynyl group" may include linear or branched $C_2$-$C_{10}$ alkynyl groups, such as ethynyl, 1-propyn-1-yl, 2-propyn-1-yl, 4-pentyn-1-yl, and 5-hexyn-1-yl.

In the present specification, unless otherwise specified, examples of the "cycloalkyl group" may include $C_3$-$C_7$ cycloalkyl groups, such as cyclopropyl, cyclobutyl, cyclopentyl, cyclohexyl, and cycloheptyl.

In the present specification, unless otherwise specified, examples of the "cycloalkenyl group" may include $C_3$-$C_7$ cycloalkenyl groups, such as cyclopropenyl, cyclobutenyl, cyclopentenyl, cyclohexenyl, and cycloheptenyl.

In the present specification, unless otherwise specified, examples of the "cycloalkadienyl group" may include $C_4$-$C_{10}$ cycloalkadienyl groups, such as cyclobutadienyl, cyclopentadienyl, cyclohexadienyl, cycloheptadienyl, cyclooctadienyl, cyclononadienyl, and cyclodecadienyl.

In the present specification, unless otherwise specified, the "aryl group" may be monocyclic, bicyclic, tricyclic, or tetracyclic.

In the present specification, unless otherwise specified, the "aryl group" may be a $C_6$-$C_{18}$ aryl group.

In the present specification, unless otherwise specified, examples of the "aryl group" may include phenyl, 1-naphthyl, 2-naphthyl, 2-biphenyl, 3-biphenyl, 4-biphenyl, and 2-anthryl.

In the present specification, unless otherwise specified, examples of the "aralkyl group" may include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

In the present specification, unless otherwise specified, the "non-aromatic heterocyclic group" may be monocyclic, bicyclic, tricyclic, or tetracyclic.

In the present specification, unless otherwise specified, the "non-aromatic heterocyclic group" may be, for example, a non-aromatic heterocyclic group containing, in addition to carbon, 1 to 4 heteroatoms selected from oxygen, sulfur, and nitrogen as a ring-constituting atom.

In the present specification, unless otherwise specified, the "non-aromatic heterocyclic group" may be saturated or unsaturated.

In the present specification, unless otherwise specified, examples of the "non-aromatic heterocyclic group" may include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, and the like.

In the present specification, unless otherwise specified, examples of the "heteroaryl group" may include monocyclic aromatic heterocyclic groups (e.g., 5- or 6-membered monocyclic aromatic heterocyclic groups) and aromatic condensed heterocyclic groups (e.g., 5- to 18-membered aromatic condensed heterocyclic groups).

In the present specification, unless otherwise specified, examples of the "5- or 6-membered monocyclic aromatic heterocyclic groups" may include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), pyrazinyl, and the like.

In the present specification, unless otherwise specified, examples of the "5- to 18-membered aromatic condensed heterocyclic groups" may include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), and the like In the present specification, examples of "R'O—" may include alkoxy (e.g., $C_1$-$C_{10}$ alkoxy, such as methoxy, ethoxy, propoxy, and butoxy), cycloalkoxy (e.g., $C_3$-$C_7$ cycloalkoxy, such as cyclopentoxy and cyclohexoxy), aryloxy (e.g., $C_6$-$C_{18}$ aryloxy, such as phenoxy and naphthoxy), and aralkyloxy (e.g., $C_7$-$C_{19}$ aralkyloxy, such as benzyloxy and phenethyloxy).

In the present specification, examples of "R'CO—" may include alkylcarbonyl (e.g., ($C_1$-$C_{10}$ alkyl)carbonyl, such as acetyl, propionyl, and butyryl), cycloalkylcarbonyl (e.g., ($C_3$-$C_7$ cycloalkyl)carbonyl, such as cyclopentanoyl and cyclohexanoyl), arylcarbonyl (e.g., ($C_6$-$C_{18}$ aryl)carbonyl, such as benzoyl and naphthoyl), and aralkylcarbonyl (e.g., ($C_7$-$C_{19}$ aralkyl)carbonyl, such as benzylcarbonyl and phenethylcarbonyl).

In the present specification, examples of "R'COO—" may include alkylcarbonyloxy (e.g., ($C_1$-$C_{10}$ alkyl)carbonyloxy, such as acetyloxy, propionyloxy, and butyryloxy), cycloalkylcarbonyloxy (e.g., ($C_3$-$C_7$ cycloalkyl)carbonyloxy, such as cyclopentanoyloxy and cyclohexanoyloxy), arylcarbonyloxy (e.g., ($C_6$-$C_{18}$ aryl)carbonyloxy, such as benzoyloxy and naphthoyloxy), and aralkylcarbonyloxy (e.g., ($C_7$-$C_{19}$ aralkyl)carbonyloxy, such as benzylcarbonyloxy and phenethylcarbonyloxy).

In the present specification, examples of "R'SO$_2$—" may include alkylsulfonyl (e.g., $C_1$-$C_{10}$ alkylsulfonyl, such as methylsulfonyl, ethylsulfonyl, and propylsulfonyl), cycloalkylsulfonyl (e.g., $C_4$-$C_8$ cycloalkylsulfonyl, such as cyclopentylsulfonyl and cyclohexylsulfonyl), arylsulfonyl (e.g., $C_6$-$C_{18}$ arylsulfonyl, such as phenylsulfonyl and naphthylsulfonyl), and aralkylsulfonyl (e.g., $C_7$-$C_{19}$ aralkylsulfonyl, such as benzylsulfonyl and phenethylsulfonyl).

In the present specification, examples of "R'OCO—" may include alkoxycarbonyl (e.g., $C_1$-$C_{10}$ alkoxy)carbonyl, such as methoxycarbonyl, ethoxycarbonyl, and propoxycarbonyl), cycloalkoxycarbonyl (e.g., ($C_3$-$C_7$ cycloalkoxy)carbonyl, such as cyclopentoxycarbonyl and cyclohexoxycarbonyl), aryloxycarbonyl (e.g., ($C_6$-$C_{18}$ aryloxy)carbonyl, such as phenoxycarbonyl and naphthoxycarbonyl), and aralkyloxycarbonyl (e.g., ($C_7$-$C_{19}$ aralkyloxy)carbonyl, such as benzyloxycarbonyl and phenethyloxycarbonyl.

In the present specification, examples of "R'OSO$_2$—" may include alkoxysulfonyl (e.g., $C_1$-$C_{10}$ alkoxysulfonyl, such as methoxysulfonyl, ethoxysulfonyl, and propoxysulfonyl), cycloalkoxysulfonyl (e.g., $C_3$-$C_7$ cycloalkoxysulfonyl, such as cyclopentoxysulfonyl and cyclohexoxysulfonyl), aryloxysulfonyl (e.g., $C_6$-$C_{18}$ aryloxysulfonyl, such as phenoxysulfonyl and naphthoxysulfonyl), and aralkyloxysulfonyl (e.g., $C_7$-$C_{19}$ aralkyloxysulfonyl, such as benzyloxysulfonyl and phenethyloxysulfonyl).

In the present specification, examples of the "substituents" in the "hydrocarbon group optionally having one or more substituents," "alkyl group optionally having one or more substituents," "alkenyl group optionally having one or more substituents," "alkynyl group optionally having one or more substituents," "cycloalkyl group optionally having one or more substituents," "cycloalkenyl group optionally having one or more substituents," "cycloalkadienyl group optionally having one or more substituents," "aryl group optionally having one or more substituents," "aralkyl group optionally having one or more substituents," "non-aromatic heterocyclic group optionally having one or more substituents," and "heteroaryl group optionally having one or more substituents" may include a halo group, a nitro group, a cyano group, an oxo group, a thioxo group, a carboxyl group, a sulfo group, a sulfamoyl group, a sulfinamoyl group, a sulfenamoyl group, R'O—, R'CO—, R'COO—, R'SO$_2$—, R'OCO—, and R'OSO$_2$— (in these formulas, R' is as defined above).

Of these substituents, examples of the "halo group" may include fluoro, chloro, bromo, and iodo.

The number of substituents may be within the range of 1 to the maximum substitutable number (e.g., 1, 2, 3, 4, 5, or 6).

Method for Producing Fluorine and Iodine Adduct of Compound (1)

The production method according to the present disclosure comprises reacting compound (1) with fluorine source (A), iodine source (B), and compound (C) to add fluorine and iodine to the double bond or triple bond of compound (1).

Reaction Substrate: Compound (1)

In compound (1), preferably, $R^1$ and $R^2$ may each be independently a hydrogen atom, a halogen atom, an alkyl group optionally having one or more substituents, an alkoxy group optionally having one or more substituents, a carboxyl group optionally having one or more substituents, a cycloalkyl group optionally having one or more substituents, an aryl group optionally having one or more substituents, or an aralkyl group optionally having one or more substituents; more preferably, $R^1$ and $R^2$ may each be independently a hydrogen atom, a halogen atom, an alkyl group optionally having one or more substituents, an alkoxy group optionally having one or more substituents, a carboxyl group optionally having one or more substituents, an aryl group optionally having one or more substituents, or an aralkyl group optionally having one or more substituents; and even more preferably, $R^1$ and $R^2$ may each be independently a hydrogen atom, a halogen atom, an alkyl group optionally having one or more substituents, an alkoxy group optionally having one or more substituents, a carboxyl group optionally having one or more substituents, or an aryl group optionally having one or more substituents.

In compound (1), it is preferred that $R^1$ and $R^2$ are each independently a hydrogen atom, a halogen atom (in particular, fluorine), an alkyl group optionally having one or more substituents, an alkoxy group optionally having one or more substituents, or a carboxyl group optionally having one or more substituents; or that $R^1$ and $R^2$ are each independently a hydrogen atom, a halogen atom (in particular, fluorine), or an aryl group optionally having one or more substituents.

When $R^1$ and $R^2$ are each an alkyl group, an alkoxy group, a cycloalkyl group, an aryl group, or an aralkyl group, preferable examples of the substituents with which these groups are optionally substituted include a halo group, a hydroxyl group, an alkoxy group, a carboxyl group, an alkylcarbonyl group, an alkylcarbonyloxy group, an alkoxycarbonyl group, and combinations thereof.

When $R^1$ and $R_2$ are each a carboxyl group, preferable examples of the substituents with which this group is optionally substituted include a halo group, an alkyl group, and combinations thereof.

Examples of the alkyl group optionally having one or more substituents include an alkyl group having halo, alkoxy, carboxyl, or a combination thereof as substituent(s) (e.g., a trifluoromethyl group, a perfluoroethyl group, a perfluoropropyl group, a perfluorobutyl group, or like perfluoroalkyl group, a perfluoro (alkoxyalky) group, or $—(CF_2)_{p1}—O—(CF_2)_{p2}—COOH$, wherein p1 and p2 are each independently an integer of 1 or more, such as $—CF_2OCF_2CF_2COOH$).

Examples of the alkoxy group optionally having one or more substituents include an alkoxy group having halo, alkoxy, carboxyl, or a combination thereof as substituent(s) (e.g., a trifluoromethoxy group, a perfluoroethoxy group, a perfluoropropoxy group, perfluorobutoxy group, or like perfluoroalkoxy group, a perfluoro(alkoxyalkoxy) group, or $—O—(CF_2)_{p3}—COOH$, wherein p3 is an integer of 1 or more, such as $—OCF_2CF_2COOH$).

Examples of the carboxyl group optionally having one or more substituents include R′OCO—. Specific examples thereof include a carboxyl group having alkyl as a substituent (e.g., a methoxycarbonyl group, an ethoxycarbonyl group, or like alkoxycarbonyl group).

In compound (1), also preferably, $R^1$ and $R^2$ may form a ring together with the two adjacent carbon atoms. The ring is formed generally when the symbol is a double bond and n is 2.

Examples of the ring include cycloalkene rings corresponding to the groups mentioned above as examples of the "cycloalkenyl group," and non-aromatic heterocyclic rings corresponding to the groups with carbon-carbon double bond(s) among the groups mentioned above as examples of the "non-aromatic heterocyclic group."

The ring optionally has one or more substituents.

Examples of the substituents may include a hydrocarbon group, a halo group, a nitro group, a cyano group, an oxo group, a thioxo group, a carboxyl group, a sulfo group, a sulfamoyl group, a sulfinamoyl group, a sulfenamoyl group, R′O—, R′CO—, R′COO—, R′SO$_2$—, R′OCO—, and R′OSO$_2$— (in these formulas, R′ is as defined above).

The number of substituents may be within the range of 1 to the maximum substitutable number (e.g., 1, 2, 3, 4, 5, or 6).

Preferable examples of compound (1) include a compound represented by formula (1a):

(1a)

wherein
$R^{11}$, $R^{12}$, $R^{21}$, and $R^{22}$ are each independently a hydrogen atom, a halogen atom, or an organic group, $R^{11}$ and $R^{12}$, or $R^{21}$ and $R^{22}$ optionally form a ring together with the adjacent carbon atom, or $R^{11}$ and $R^{21}$, $R^{11}$ and $R^{22}$, $R^{12}$ and $R^{21}$, or $R^{12}$ and $R^{22}$ optionally form a ring together with the two adjacent carbon atoms;
the symbol ⁓⁓⁓ indicates a cis configuration or a trans configuration; and
a compound represented by formula (1b):

(1b)

wherein $R^{13}$ and $R^{23}$ are each independently a hydrogen atom, a halogen atom, or an organic group.

In one embodiment of compound (1a), preferably, $R^{11}$, $R^{12}$, and $R^{21}$ are each independently a hydrogen atom, a halogen atom, an alkyl group optionally having one or more substituents, an alkoxy group optionally having one or more substituents, a carboxyl group optionally having one or more substituents, a cycloalkyl group optionally having one or more substituents, an aryl group optionally having one or more substituents, or an aralkyl group optionally having one or more substituents, and $R^{22}$ is a hydrogen atom. More preferably, $R^{11}$, $R^{12}$, and $R^{21}$ are each independently a hydrogen atom, a halogen atom, an alkyl group optionally having one or more substituents, an alkoxy group optionally having one or more substituents, a carboxyl group optionally having one or more substituents, or an aryl group optionally having one or more substituents, and $R^{22}$ is a hydrogen atom.

In another embodiment of compound (1a), preferably, $R^{11}$ and $R^{21}$ are each independently a hydrogen atom, a halogen atom, an alkyl group optionally having one or more substituents, an alkoxy group optionally having one or more substituents, a carboxyl group optionally having one or more substituents, a cycloalkyl group optionally having one or more substituents, an aryl group optionally having one or more substituents, or an aralkyl group optionally having one or more substituents, and $R^{12}$ and $R^{22}$ are hydrogen atoms; more preferably, $R^{11}$ and $R^{21}$ are each independently a hydrogen atom, a halogen atom, an alkyl group optionally having one or more substituents, an alkoxy group optionally having one or more substituents, a carboxyl group optionally having one or more substituents, an aryl group optionally having one or more substituents, or an aralkyl group optionally having one or more substituents, and $R^{12}$ and $R^{22}$ are hydrogen atoms; and even more preferably, $R^{11}$ and $R^{21}$ are each independently a hydrogen atom, a halogen atom, an alkyl group optionally having one or more substituents, an alkoxy group optionally having one or more substituents, a carboxyl group optionally having one or more substituents, or an aryl group optionally having one or more substituents, and $R^{12}$ and $R^{22}$ are hydrogen atoms.

In this embodiment, it is preferred that $R^{11}$ and $R^{12}$ are each independently a hydrogen atom, a halogen atom, an alkyl group optionally having one or more substituents, an alkoxy group optionally having one or more substituents, or a carboxyl group optionally having one or more substituents, and $R^{12}$ and $R^{22}$ are hydrogen atoms; or that $R^{11}$ and $R^{12}$ are each independently a hydrogen atom, a halogen atom, or an aryl group optionally having one or more substituents, and $R^{12}$ and $R^{22}$ are hydrogen atoms.

In another embodiment of compound (1a), preferably, $R^{11}$ is a hydrogen atom, a halogen atom, an alkyl group optionally having one or more substituents, an alkoxy group optionally having one or more substituents, a carboxyl group optionally having one or more substituents, or an aryl group optionally having one or more substituents, and $R^{12}$, $R^{21}$, and $R^{22}$ are hydrogen atoms; and more preferably, $R^{11}$ is a hydrogen atom, a halogen atom (in particular, fluorine), an alkyl group optionally having one or more substituents, an alkoxy group optionally having one or more substituents, or a carboxyl group optionally having one or more substituents, and $R^{12}$, $R^{21}$, and $R^{22}$ are hydrogen atoms.

Preferable examples of the substituents in $R^{11}$, $R^{12}$, $R^{21}$, and $R^{22}$ include those mentioned above as examples of the substituents in $R^1$ and $R^2$.

Examples of the alkyl group optionally having one or more substituents include an alkyl group having halo, alkoxy, carboxyl, or a combination thereof as substituent(s) (e.g., a trifluoromethyl group, a perfluoroethyl group, a perfluoropropyl group, a perfluorobutyl group, or like perfluoroalkyl group, a perfluoro (alkoxyalky) group, or —$(CF_2)_{p1}$—O—$(CF_2)_{p2}$—COOH, wherein p1 and p2 are each independently an integer of 1 or more, such as —$CF_2OCF_2CF_2COOH$).

Examples of the alkoxy group optionally having one or more substituents include an alkoxy group having halo, alkoxy, carboxyl, or a combination thereof as substituent(s) (e.g., a trifluoromethoxy group, a perfluoroethoxy group, a perfluoropropoxy group, a perfluorobutoxy group, or like perfluoroalkoxy group; a perfluoro(alkoxyalkoxy) group; or —O—$(CF_2)_{p3}$—COOH, wherein p3 is an integer of 1 or more, such as —$OCF_2CF_2COOH$).

Examples of the carboxyl group optionally having one or more substituents include R'OCO—. Specific examples thereof include a carboxyl group having alkyl as a substituent (e.g., a methoxycarbonyl group, an ethoxycarbonyl group, or like alkoxycarbonyl group).

In compound (1a), also preferably, $R^{11}$ and $R^{21}$ form a ring together with the two adjacent carbon atoms, and $R^{12}$ and $R^{22}$ are hydrogen atoms.

Examples of the ring include cycloalkene rings corresponding to the groups mentioned above as examples of the "cycloalkenyl group" (e.g., a $C_5$-$C_7$ cycloalkene ring, such as a cyclohexene ring), and non-aromatic heterocyclic rings corresponding to the groups with carbon-carbon double bond(s) among the groups mentioned above as examples of the "non-aromatic heterocyclic group."

The ring optionally has one or more substituents.

Examples of the substituents may include a hydrocarbon group, a halo group, a nitro group, a cyano group, an oxo group, a thioxo group, a carboxyl group, a sulfo group, a sulfamoyl group, a sulfinamoyl group, a sulfenamoyl group, R'O—, R'CO—, R'COO—, R'SO₂—, R'OCO—, and R'OSO₂— (in these formulas, RE is as defined above).

The number of substituents may be within the range of 1 to the maximum substitutable number (e.g., 1, 2, 3, 4, 5, or 6).

Specific examples of compound (1a) include olefins (e.g., pentene, hexene, heptene, octene, nonene, decene, undecene, and dodecene), alkenols (e.g., allyl alcohol, butenol, pentenol, hexenol, heptenol, octenol, nonenol, decenol, undecenol, and dodecenol), alkenoic acid (e.g., acrylic acid, methacrylic acid, crotonic acid, isocrotonic acid, pentenoic acid, hexenoic acid, heptenoic acid, octenoic acid, nonenoic acid, decenoic acid, undecenoic acid, and dodecenoic acid) or esters thereof (e.g., alkyl esters, such as methyl ester), fluorinated olefins (e.g., vinylidene fluoride, trifluoroethylene, chlorotrifluoroethylene, tetrafluoroethylene, and hexafluoropropylene), fluoroalkyl vinyl ethers (e.g., perfluoroalkyl vinyl ethers, such as perfluoromethyl vinyl ether, perfluoroethyl vinyl ether, and perfluoropropyl vinyl ether), aryl olefins (e.g., styrene, methylstyrene, stilbene, diphenylethylene, triphenylethylene, methyl cinnamate, ethyl cinnamate, and allylbenzene), and cycloolefins (e.g., cyclohexene).

In compound (1b), preferably, $R^{13}$ and $R^{23}$ are each independently a hydrogen atom, a halogen atom, an alkyl group optionally having one or more substituents, an alkoxy group optionally having one or more substituents, a carboxyl group optionally having one or more substituents, a cycloalkyl group optionally having one or more substituents, an aryl group optionally having one or more substituents, or an aralkyl group optionally having one or more substituents; more preferably, $R^{13}$ and $R^{23}$ are each independently a hydrogen atom, a halogen atom, an alkyl group optionally having one or more substituents, an alkoxy group optionally having one or more substituents, a carboxyl group optionally having one or more substituents, an aryl group optionally having one or more substituents, or an aralkyl group optionally having one or more substituents; and even more preferably, $R^{13}$ and $R^{23}$ are each independently a hydrogen atom, a halogen atom (in particular, fluorine), an alkyl group optionally having one or more substituents, an alkoxy group optionally having one or more substituents, or a carboxyl group optionally having one or more substituents.

Preferable examples of the substituents in $R^{13}$ and $R^{23}$ include those mentioned above as examples of the substituents in $R^1$ and $R^2$.

Examples of the alkyl group optionally having one or more substituents include an alkyl group having halo, alkoxy, carboxyl, or a combination thereof as substituent(s) (e.g., a trifluoromethyl group, a perfluoroethyl group, a perfluoropropyl group, a perfluorobutyl group, or like perfluoroalkyl group, a perfluoro(alkoxyalky) group, or —$(CF_2)_{p1}$—O—$(CF_2)_{p2}$—COOH, wherein p1 and p2 are each independently an integer of 1 or more, such as —$CF_2OCF_2CF_2COOH$.

Examples of the alkoxy group optionally having one or more substituents include an alkoxy group having halo, alkoxy, carboxyl, or a combination thereof as substituent(s) (e.g., a trifluoromethoxy group, a perfluoroethoxy group, a perfluoropropoxy group, a perfluorobutoxy group, or like perfluoroalkoxy group, a perfluoro(alkoxyalkoxy) group, or —O—$(CF_2)_{p3}$—COOH, wherein p3 is an integer of 1 or more, such as —$OCF_2CF_2COOH$).

Examples of the carboxyl group optionally having one or more substituents include R'OCO—. Specific examples thereof include a carboxyl group having alkyl as a substituent (e.g., a methoxycarbonyl group, an ethoxycarbonyl group, or like alkoxycarbonyl group).

Fluorine Source (A)

Of fluorine sources (A), hydrogen fluoride may be used as an aqueous solution (hydrofluoric acid). The aqueous solution may be, for example, an aqueous solution having a hydrogen fluoride concentration of 10 to 70 wt %.

Of fluorine sources (A), examples of hydrogen fluoride salts include hydrogen fluoride amine salts and hydrogen fluoride ammonium salts.

In the hydrogen fluoride amine salts, the amine may be a chain amine or a cyclic amine.

Examples of chain amines include aliphatic primary amines, aliphatic secondary amines, and aliphatic tertiary amines.

Examples of aliphatic primary amines include $C_1$-$C_6$ alkylamines, such as methylamine, ethylamine, propylamine, butylamine, pentylamine, and hexylamine.

Examples of aliphatic secondary amines include di-$C_1$-$C_6$ alkylamines, such as dimethylamine, diethylamine, dipropylamine, dibutylamine, dipentylamine, and dihexylamine.

Examples of aliphatic tertiary amines include tri-$C_1$-$C_6$ alkylamines, such as trimethylamine, triethylamine, diisopropylethylamine, tributylamine, and N,N,N',N'-tetramethylethylenediamine.

Examples of cyclic amines include aliphatic cyclic amines and aromatic cyclic amines.

Examples of aliphatic cyclic amines include piperidine, piperazine, pyrrolidine, morpholine, N-methylpiperazine, N-methylpyrrolidine, 5-diazabicyclo[4.3.0]non-5-ene, and 1,4-diazabicyclo[2.2.2]octane.

Examples of aromatic cyclic amines include pyridine, pyrimidine, pyrazine, quinoline, and imidazole.

Examples of hydrogen fluoride ammonium salts include ammonium hydrogen fluoride ($NH_4F·HF$), hydrogen fluoride-tetraethylammonium fluoride [$Et_4NF·xHF$ (x=1 to 10)], and hydrogen fluoride-tetrabutylammonium fluoride [$Bu_4NF·xHF$ (x=1 to 10)].

Preferable examples of hydrogen fluoride salts include hydrogen fluoride amine salts. More preferable examples thereof include hydrogen fluoride-triethylamine salt [$Et_3N·xHF$ (x=1 to 5)] and hydrogen fluoride-pyridine salt [$Py·xHF$ (x=1 to 10)].

Of fluorine sources (A), examples of fluoride salts include a compound represented by formula: $M^1F_{m1}$, wherein $M^1$ is an alkali metal or an alkaline earth metal; and m1 is 1 or 2.

$M^1$ may be preferably Li, Na, K, Ca, or Cs, more preferably Na, K, or Ca, and even more preferably K.

The fluoride salts may be preferably alkali metal fluoride salts (compounds in which $M^1$ is an alkali metal, and m1 is 1).

Fluorine sources (A) may be used singly, or in a combination of two or more.

The amount of fluorine source (A) used may be, for example, within the range of 0.1 to 1000 moles, preferably 0.2 to 500 moles, more preferably 0.3 to 100 moles, even more preferably 0.4 to 50 moles, and still even more preferably 0.5 to 10 moles, per mole of compound (1).

Fluorine source (A) remaining after the reaction may be trapped and discarded; however, it is preferable to recover and reuse it from the viewpoint of production cost. The trapped residue after the reaction may be washed with, for example, water or alkaline water.

Iodine Source (B)

Of iodine sources (B), examples of iodide salts include tetraalkylammonium iodides and compounds represented by formula: $M^2I_{m2}$, wherein $M^2$ is an alkali metal or an alkaline earth metal; and m2 is 1 or 2).

Examples of tetraalkylammonium iodides include tetra-$C_1$-$C_6$ alkylammonium iodides, such as tetramethylammonium iodide, tetraethylammonium iodide, ethyltrimethylammonium iodide, and tetrabutylammonium iodide.

$M^2$ may be preferably Li, Na, K, Ca, or Cs; more preferably Na, K, or Ca; and even more preferably K.

Iodine source (B) may be preferably at least one member selected from the group consisting of iodine and alkali metal iodide salts (compounds in which $M^2$ is an alkali metal, and m2 is 1).

Iodine sources (B) may be used singly, or in a combination of two or more.

The amount of iodine source (B) used may be, for example, within the range of 0.1 to 10 moles, preferably 0.2 to 9 moles, more preferably 0.3 to 8 moles, even more preferably 0.4 to 7 moles, and still even more preferably 0.5 to 6 moles, per mole of compound (1).

Iodine source (B) remaining after the reaction may be trapped and discarded; however, it is preferable to recover and reuse it from the viewpoint of production cost. The trapped residue after the reaction may be washed with, for example, water or alkaline water.

Compound (C)

Compound (C) is not limited and may be, for example, at least one member selected from the group consisting of
(i) peroxides,
(ii) metal oxides,
(iii) azo compounds,
(iv) sulfonium salts, and
(v) iodonium salts.

Peroxides (i) may be inorganic peroxides or organic peroxides.

Examples of inorganic peroxides include hydrogen peroxide; and perboric acid, percarbonic acid, perphosphoric acid, persulfuric acid, perchloric acid, permanganic acid, and salts thereof (e.g., alkali metal salts, such as ammonium salts, sodium salts, and potassium salts). These salts may be hydrates. Examples of persulfates include a potassium hydrogen persulfate-potassium hydrogen sulfate-potassium sulfate mixture.

Examples of organic peroxides include (i-a) a compound represented by formula: $R^aCOOOM$, wherein
  $R^a$ is a hydrocarbon group optionally having one or more substituents; and M is a hydrogen atom or a metal atom;
  (i-b) a compound represented by formula: $R^bOOM$, wherein
  $R^b$ is a hydrocarbon group optionally having one or more substituents; and M is a hydrogen atom or a metal atom;
  (i-c) a compound represented by formula: $R^{c1}OOR^{c2}$, wherein
  $R^{c1}$ and $R^{c2}$ are each independently a hydrocarbon group optionally having one or more substituents or $R^{c3}$—CO—, and $R^{c3}$ is a hydrocarbon group optionally having one or more substituents; and (i-d) a compound represented by formula:

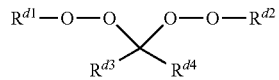

wherein

R$^{d1}$ and R$^{d4}$ are each independently a hydrocarbon group optionally having one or more substituents, and R$^{d3}$ and R$^{d4}$ optionally form a ring together with the adjacent carbon atom.

Examples of compound (i-a) include performic acid, peracetic acid, trifluoroperacetic acid, perpropionic acid, perbenzoic acid, and metachloroperbenzoic acid.

Examples of compound (i-b) include alkyl hydroperoxides, such as tert-butyl hydroperoxide; and aralkyl hydroperoxides, such as cumene hydroperoxide.

Examples of compound (i-c) include dialkyl peroxides, such as di-tert-butyl peroxide; diaralkyl peroxides, such as dicumyl peroxide; di(alkylcarbonyl)peroxides, such as diisobutyryl peroxide, and di(arylcarbonyl)peroxide, such as dibenzoyl peroxide.

Examples of compound (i-d) include di(alkylperoxy)alkanes, such as 2,2-di(t-butylperoxy)butane; and di(alkylperoxy)cycloalkanes, such as 1,1-di(t-butylperoxy)cyclohexane and 1,1-di(t-hexylperoxy)cyclohexane.

Examples of metal oxides (ii) include chromic acid, dichromic acid, tungsten oxide, ruthenium oxide, antimony oxide, osmium oxide, and sulfur trioxide.

Examples of azo compounds (iii) include azonitrile compounds, azoester compounds, azoamide compounds, azoamidine compounds, and azoimidazoline compounds.

Examples of azonitrile compounds include 2,2'-azobis(isobutyronitrile), 2,2'-azobis(2-methylbutyronitrile), 4,4'-azobis(4-cyanovaleric acid), 2,2'-azobis(2,4-dimethylvaleronitrile), 2,2'-azobis(4-methoxy-2,4-dimethylvaleronitrile), and 1,1'-azobis(cyclohexane-1-carbonitrile).

Examples of azoester compounds include 2,2'-azobis(methyl 2-methylpropionate) and 1,1'-azobis(methyl 1-cyclohexanecarboxylate).

Examples of azoamide compounds include 2,2'-azobis(N-butyl-2-methylpropionamide) and 2,2'-azobis[2-methyl-N-(2-hydroxyethyl)propionamide].

Examples of azoamidine compounds include 2,2'-azobis(2-methylpropionamide) and 2,2'-azobis[N-(2-carboxyethyl)-2-methylpropionamide].

Examples of azoimidazoline compounds include 2,2'-azobis[2-(2-imidazolin-2-yl)propane].

Examples of sulfonium salts (iv) include triarylsulfonium salts. Preferable examples thereof include triphenylsulfonium salt, diphenyl(4-methylphenyl)sulfonium salt, diphenyl(2,4,6-trimethylphenyl)sulfonium salt, diphenyl(4-methoxyphenyl)sulfonium salt, tris(4-methylphenyl)sulfonium salt, and diphenyl[4-(phenylthio)phenyl]sulfonium salt.

Examples of iodonium salts (v) include bisaryliodonium salts. Preferable examples thereof include diphenyliodonium salt, bis(4-tert-butylphenyl)iodonium salt, bis(4-tert-butylphenyl) iodonium salt, and bis[4-alkyl (C$_{10-13}$)phenyl] iodonium salt.

The anions in sulfonium salts (iv) or iodonium salts (v) may be, for example, trifluoromethanesulfonate ion, nonafluorobutanesulfonate ion, p-toluenesulfonate ion, tetrafluoroboronate ion, tetrakis pentafluorophenylboronate ion, hexafluorophosphate ion, or hexafluoroantimonate ion.

Preferable examples of compound (C) include hydrogen peroxide, peracetic acid, perbenzoic acid, metachloroperbenzoic acid, tert-butyl hydroperoxide, cumene hydroperoxide, sodium perborate, potassium persulfate, a potassium hydrogen persulfate-potassium hydrogen sulfate-potassium sulfate mixture, permanganic acid, dichromic acid, tungsten oxide, ruthenium oxide, antimony oxide, osmium oxide, and sulfur trioxide.

More preferable examples of compound (C) include hydrogen peroxide, peracetic acid, perbenzoic acid, metachloroperbenzoic acid, tert-butyl hydroperoxide, cumene hydroperoxide, sodium perborate, potassium persulfate, and a potassium hydrogen persulfate-potassium hydrogen sulfate-potassium sulfate mixture.

Compounds (C) may be used singly, or in a combination of two or more.

The amount of compound (C) used may be, for example, within the range of 0.1 to 10 moles, preferably 0.1 to 8 moles, more preferably 0.1 to 5 moles, and even more preferably 0.1 to 3 moles, per mole of compound (1).

IF$_5$

The reaction in the above step may be performed in the presence or absence of IF$_5$, and it is preferred that the reaction is performed in the absence of IF$_5$.

Each component may be added to the reaction system of the step A all at once, in several batches, or continuously.

Solvent

The reaction of the above step may be performed in the presence or absence of a solvent.

The solvent may be a nonpolar solvent or a polar solvent.

Examples of the solvent include esters, ketones, aromatic hydrocarbons, alcohols, ethers, amines, nitrogen-containing polar organic compounds, nitriles, halogenated hydrocarbons, aliphatic hydrocarbons, fluorine-based solvents, carbonates, other solvents, and combinations thereof.

Examples of esters as the solvent include ethyl acetate, butyl acetate, amyl acetate, ethylene glycol monomethyl ether acetate, and propylene glycol monomethyl ether acetate; and preferably ethyl acetate.

Examples of ketones as the solvent include acetone, methyl ethyl ketone, diethyl ketone, hexanone, methyl isobutyl ketone, heptanone, diisobutyl ketone, acetonylacetone, methylhexanone, acetophenone, cyclohexanone, and diacetone alcohol; and preferably acetone.

Examples of aromatic hydrocarbons as the solvent include benzene, toluene, xylene, and ethylbenzene; and preferably benzene and toluene.

Examples of alcohols as the solvent include methanol, ethanol, n-propanol, isopropanol, n-butanol, pentanol, hexanol, ethylene glycol, diethylene glycol, triethylene glycol, tetraethylene glycol, polyethylene glycol, propylene glycol, dipropylene glycol, tripropylene glycol, polypropylene glycol, trimethylene glycol, and hexanetriol; and preferably methanol and ethanol.

Examples of ethers as the solvent include diethyl ether, dibutyl ether, tetrahydrofuran, tetrahydropyran, dioxane, dimethoxyethane, diethylene glycol diethyl ether, ethylene glycol monomethyl ether, ethylene glycol monoethyl ether, diethylene glycol monomethyl ether, diethylene glycol monoethyl ether, propylene glycol monomethyl ether (PGME; also known as "1-methoxy-2-propanol"), propylene glycol monoethyl ether, triethylene glycol dimethyl ether, triethylene glycol diethyl ether, tetraethylene glycol dimethyl ether, tetraethylene glycol diethyl ether, and anisole; and preferably diethyl ether and tetrahydrofuran.

Examples of amines as the solvent include monoethanolamine, diethanolamine, and triethanolamine.

Examples of nitrogen-containing polar organic compounds as the solvent include N,N-dimethylformamide, N,N-dimethylacetamide, N-methyl-2-pyrrolidone, 2-pyrrolidone, and 1,3-dimethyl-2-imidazolidinone; and preferably N,N-dimethylformamide, N,N-dimethylacetamide, and N-methyl-2-pyrrolidone.

Examples of nitriles as the solvent include acetonitrile, propionitrile, butyronitrile, isobutyronitrile, benzonitrile, and adiponitrile; and preferably acetonitrile.

Examples of halogenated hydrocarbons as the solvent include dichloromethane, dichloroethane, chloroform, carbon tetrachloride, tetrachloroethane, trichloroethane, chlorobenzene, dichlorobenzene, and chlorotoluene; and preferably dichloromethane and chloroform.

Examples of aliphatic hydrocarbons as the solvent include hexane, cyclohexane, heptane, octane, nonane, decane, undecane, dodecane, and mineral spirits; and preferably cyclohexane and heptane.

Examples of fluorine-based solvents include perfluorobenzene, trifluorotoluene, ditrifluorobenzene, and trifluoroethanol; and preferably perfluorobenzene and trifluoroethanol.

Examples of carbonates as the solvent include tetralin dimethyl carbonate, methyl ethyl carbonate, diethyl carbonate, ethylene carbonate, and propylene carbonate; and preferably ethylene carbonate and propylene carbonate.

Examples of other solvents include acetic acid, pyridine, dimethylsulfoxide, sulfolane, and water.

The solvent may be preferably at least one member selected from the group consisting of aliphatic hydrocarbons, aromatic hydrocarbons, halogenated hydrocarbons, ethers, esters, nitriles, and water, more preferably at least one member selected from the group consisting of aliphatic hydrocarbons, halogenated hydrocarbons, ethers, and water, and even more preferably a halogenated hydrocarbon.

These solvents may be used singly, or in a combination of two or more.

The amount of solvent used may be, for example, generally within the range of 0 to 200 parts by mass, preferably within the range of 0 to 100 parts by mass, and more preferably within the range of 0 to 50 parts by mass, per part by mass of compound (1).

Temperature and Time

The temperature of the above step may be generally within the range of −78 to 200° C., preferably within the range of −10 to 100° C., more preferably within the range of 0 to 100° C., and even more preferably within the range of 10 to 40° C.

The time of the above step may be generally within the range of 0.1 to 72 hours, preferably within the range of 0.5 to 48 hours, and more preferably within the range of 1 to 36 hours.

Product: Fluorine and Iodine Adduct of Compound (1)

A fluorine and iodine adduct of compound (1) can be obtained as described above.

The fluorine and iodine adduct encompasses one in which one fluorine and one iodine are added to compound (1); and when compound (1) is compound (1b), the fluorine and iodine adduct encompasses one in which two fluorine and two iodine are added to compound (1b).

The fluorine and iodine adduct in which one fluorine and one iodine are added to compound (1) may be represented by formula (2):

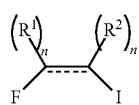

(2)

wherein
R$^1$, R$^2$, and n are as defined above; and
the symbol ≡ is a single bond or a double bond,
with the proviso that
when the symbol is a double bond, n is 1, and
when the symbol is a single bond, n is 2.

Preferable examples of compound (2) include a compound represented by formula (2a):

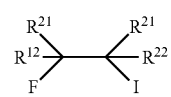

(2a)

wherein
R$^{11}$, R$^{12}$, R$^{21}$, and R$^{22}$ are as defined above, and
a compound represented by formula (2b):

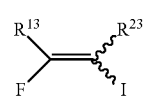

(2b)

wherein R$^{13}$ and R$^{23}$ are as defined above; and the symbol ~~~~~ indicates a cis configuration or a trans configuration.

The fluorine and iodine adduct of compound (1) obtained in this manner can be isolated or purified, if desired, by a conventional method, such as filtration, extraction, dissolution, concentration, precipitation, dehydration, adsorption, or chromatography; or a combination of these methods.

The present disclosure includes the following embodiments.

Item 1.

A method for producing a fluorine and iodine adduct of a compound represented by formula (1):

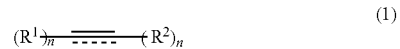

(1)

wherein
R$^1$ and R$^2$ are each independently a hydrogen atom, a halogen atom, or an organic group, or R$^1$ and R$^2$ optionally form a ring together with the two adjacent carbon atoms;
n is 1 or 2; and
the symbol

is a double bond or a triple bond,
with the proviso that
when the symbol is a triple bond, n is 1,
when the symbol is a double bond, n is 2,
two R$^1$s are optionally the same or different,
two R$^2$s are optionally the same or different, or
two R$^1$s or two R$^2$s optionally form a ring together with their adjacent carbon atom,
the method comprising reacting the compound represented by formula (1) with (A) at least one fluorine source selected from the group consisting of hydrogen fluoride, hydrogen fluoride salts, and fluoride salts,
(B) at least one iodine source selected from the group consisting of iodine and iodide salts, and
(C) at least one compound selected from the group consisting of oxidizing agents and radical generators, to add fluorine and iodine to the double bond or triple bond.

Item 2.

The production method according to Item 1, wherein the fluorine source is at least one member selected from the group consisting of hydrogen fluoride, hydrogen fluoride amine salts, and alkali metal fluoride salts.

Item 3.

The production method according to Item 1 or 2, wherein the amount of the fluorine source is within the range of 0.1 to 1000 moles, per mole of the compound represented by formula (1).

Item 4.

The production method according to any one of Items 1 to 3, wherein the iodine source is at least one member selected from the group consisting of iodine and alkali metal iodide salts.

Item 5.

The production method according to any one of Items 1 to 4, wherein the amount of the iodine source is within the range of 0.1 to 10 moles, per mole of the compound represented by formula (1).

Item 6.

The production method according to any one of Items 1 to 5, wherein the compound (C) is at least one member selected from the group consisting of peroxides, metal oxides, azo compounds, sulfonium salts, and iodonium salts.

Item 7.

The production method according to any one of Items 1 to 6, wherein the compound (C) is a peroxide.

Item 8.

The production method according to Item 7, wherein the peroxide is at least one member selected from the group consisting of hydrogen peroxide;
perboric acid, percarbonic acid, perphosphoric acid, persulfuric acid, perchloric acid, permanganic acid, and salts thereof;
compounds represented by formula: $R^{a}COOOM$, wherein $R^{a}$ is a hydrocarbon group optionally having one or more substituents, and M is a hydrogen atom or a metal atom;
compounds represented by formula: $R^{b}OOM$, wherein $R^{b}$ is a hydrocarbon group optionally having one or more substituents, and M is a hydrogen atom or a metal atom;
compounds represented by formula: $R^{c1}OOR^{c2}$, wherein $R^{c1}$ and $R^{c2}$ are each independently a hydrocarbon group optionally having one or more substituents or $R^{c3}$—CO—, and $R^{c3}$ is a hydrocarbon group optionally having one or more substituents; and compounds represented by formula:

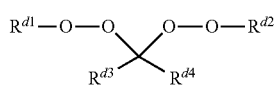

wherein $R^{d1}$ to $R^{d4}$ are each independently a hydrocarbon group optionally having one or more substituents, and $R^{d3}$ and $R^{d4}$ optionally form a ring together with the adjacent carbon atom.

Item 9.

The production method according to any one of Items 1 to 6, wherein the compound (C) is at least one member selected from the group consisting of hydrogen peroxide, peracetic acid, perbenzoic acid, metachloroperbenzoic acid, tert-butyl hydroperoxide, cumene hydroperoxide, sodium perborate, potassium persulfate, a potassium hydrogen persulfate-potassium hydrogen sulfate-potassium sulfate mixture, permanganic acid, dichromic acid, tungsten oxide, ruthenium oxide, antimony oxide, osmium oxide, and sulfur trioxide.

Item 10.

The production method according to any one of Items 1 to 9, wherein the amount of the compound (C) is within the range of 0.1 to 10 moles, per mole of the compound represented by formula (1).

Item 11.

The production method according to any one of Items 1 to 10, wherein the reaction is performed in the presence of a solvent.

Item 12.

The production method according to Item 11, wherein the solvent is at least one member selected from the group consisting of aliphatic hydrocarbons, aromatic hydrocarbons, halogenated hydrocarbons, ethers, esters, nitriles, and water.

Item 13.

The production method according to Item 11 or 12, wherein the solvent is at least one member selected from the group consisting of aliphatic hydrocarbons, halogenated hydrocarbons, ethers, and water.

Item 14.

The production method according to any one of Items 1 to 13, wherein the reaction is performed in the absence of $IF_5$.

Item 15.

The production method according to any one of Items 1 to 14, wherein the reaction is performed at room temperature for 1 to 36 hours.

Item 16.

The production method according to any one of Items 1 to 15, wherein $R^1$ and $R^2$ are each independently a hydrogen atom, a halogen atom, an alkyl group optionally having one or more substituents, an alkoxy group optionally having one or more substituents, a carboxyl group optionally having one or more substituents, a cycloalkyl group optionally having one or more substituents, an aryl group optionally having one or more substituents, or an aralkyl group optionally having one or more substituents, or $R^1$ and $R^2$ optionally form a ring together with the two adjacent carbon atoms.

Item 17.

The production method according to Item 16, wherein the one or more substituents in the alkyl, alkoxy, cycloalkyl, aryl, or aralkyl group are at least one member selected from the group consisting of halo, hydroxyl, alkoxy, carboxyl, alkylcarbonyl, alkylcarbonyloxy, and alkoxycarbonyl groups, and the one or more substituents in the carboxyl group are at least one member selected from the group consisting of halo and alkyl groups.

EXAMPLES

One embodiment of the present disclosure is described in more detail below with reference to Examples; however, the present disclosure is not limited thereto.

Example 1

An HF/Py complex (HF: 30 mmol) was added to iodine (1 mmol) and dichloromethane. Thereafter, potassium persulfate (1 mmol) and methyl 10-undecenoate (1 mmol) were added thereto, and the mixture was stirred at room temperature for 24 hours. After the reaction, quenching, liquid separation, and silica gel column purification were performed, thereby obtaining methyl 10-fluoro-11-iodoundecanoate in a yield of 70% as a target product.

Example 2

The same procedure as in Example 1 was performed, except that cyclohexene was used in place of methyl 10-undecenoate, thereby obtaining 1-fluoro-2-iodocyclohexane in a yield of 30% as a target product.

Example 3

The same procedure as in Example 1 was performed, except that trans-stilbene was used in place of methyl 10-undecenoate, thereby obtaining (1-fluoro-2-iodoethane-1,2-diyl)dibenzene in a yield of 21% as a target product.

Example 4

The same procedure as in Example 1 was performed, except that 1-dodecene was used in place of methyl 10-undecenoate, thereby obtaining 2-fluoro-1-iododdecane in a yield of 73% as a target product.

Example 5

The same procedure as in Example 1 was performed, except that 1-octene was used in place of methyl 10-undecenoate, thereby obtaining 2-fluoro-1-iodooctane in a yield of 57% as a target product.

Example 6

The same procedure as in Example 1 was performed, except that 10-undecen-1-ol was used in place of methyl 10-undecenoate, thereby obtaining 10-fluoro-11-iodoundecan-1-ol in a yield of 13% as a target product.

Example 7

The same procedure as in Example 1 was performed, except that triphenylethylene was used in place of methyl 10-undecenoate, thereby obtaining 1-fluoro-2-iodo-1,1,2-triphenylethane in a yield of 63% as a target product.

Example 8

The same procedure as in Example 1 was performed, except that ethyl cinnamate was used in place of methyl 10-undecenoate, thereby obtaining ethyl 3-fluoro-2-iodo-3-phenylpropanoate in a yield of 53% as a target product.

Example 9

The same procedure as in Example 1 was performed, except that allylbenzene was used in place of methyl 10-undecenoate, thereby obtaining (2-fluoro-3-iodopropyl)benzene in a yield of 50% as a target product.

Example 10

An HF/Py complex (HF: 30 mmol) was added to iodine (0.5 mmol) and ethyl acetate. Thereafter, potassium persulfate (2 mmol) and methyl 10-undecenoate (1 mmol) were added thereto, and the mixture was stirred at room temperature for 24 hours. After the reaction, quenching, liquid separation, and silica gel column purification were performed, thereby obtaining methyl 10-fluoro-11-iodoundecanoate in a yield of 9% as a target product.

Example 11

The same procedure as in Example 10 was performed, except that acetonitrile was used in place of ethyl acetate, thereby obtaining methyl 10-fluoro-11-iodoundecanoate in a yield of 9% as a target product.

Example 12

The same procedure as in Example 10 was performed, except that diethyl ether was used in place of ethyl acetate, thereby obtaining methyl 10-fluoro-11-iodoundecanoate in a yield of 11% as a target product.

Example 13

The same procedure as in Example 10 was performed, except that hexane was used in place of ethyl acetate, thereby obtaining methyl 10-fluoro-11-iodoundecanoate in a yield of 26% as a target product.

Example 14

The same procedure as in Example 10 was performed, except that toluene was used in place of ethyl acetate, thereby obtaining methyl 10-fluoro-11-iodoundecanoate in a yield of 4% as a target product.

Example 15

The same procedure as in Example 10 was performed, except that dichloromethane was used in place of ethyl acetate, thereby obtaining methyl 10-fluoro-11-iodoundecanoate in a yield of 40% as a target product.

Example 16

The same procedure as in Example 15 was performed, except that Oxone (a potassium hydrogen persulfate-potassium hydrogen sulfate-potassium sulfate mixture) (0.5 mmol) was used in place of potassium persulfate (2 mmol), thereby obtaining methyl 10-fluoro-11-iodoundecanoate in a yield of 49% as a target product.

Example 17

The same procedure as in Example 15 was performed, except that mCPBA (metachloroperbenzoic acid) (0.5 mmol) was used in place of potassium persulfate (2 mmol), thereby obtaining methyl 10-fluoro-11-iodoundecanoate in a yield of 47% as a target product.

Example 18

The same procedure as in Example 15 was performed, except that $NaBO_3 \cdot 4H_2O$ (0.5 mmol) was used in place of potassium persulfate (2 mmol), thereby obtaining methyl 10-fluoro-11-iodoundecanoate in a yield of 32% as a target product.

Example 19

The same procedure as in Example 15 was performed, except that 30% H₂O₂ (1.0 mmol) was used in place of potassium persulfate (2 mmol), thereby obtaining methyl 10-fluoro-11-iodoundecanoate in a yield of 48% as a target product.

Example 20

The same procedure as in Example 1 was performed, except that ethene-1,1-diyldibenzene was used in place of methyl 10-undecenoate, thereby obtaining (1-fluoro-2-iodo-ethane-1,1-diyl)dibenzene in a yield of 37% as a target product.

Example 21

The same procedure as in Example 1 was performed, except that octyl acrylate was used in place of methyl 10-undecenoate, thereby obtaining octyl 3-fluoro-2-iodo-propanoate in a yield of 39% as a target product.

Example 22

An HF/Py complex (HF: 30 mmol) was added to iodine (1 mmol) and dichloroethane. Thereafter, sodium persulfate (1 mmol) and methyl cinnamate (1 mmol) were added thereto, and the mixture was stirred at room temperature for 1 hour. After the reaction, quenching, liquid separation, and silica gel column purification were performed, thereby obtaining ethyl 3-fluoro-2-iodo-3-phenylpropanoate in a yield of 75% as a target product.

Example 23

An HF/Py complex (HF: 30 mmol) was added to iodine (1 mmol) and dichloromethane. Thereafter, potassium persulfate (1 mmol) and 1-dodecyne (1 mmol) were added thereto, and the mixture was stirred at room temperature for 24 hours. After the reaction, quenching, liquid separation, and silica gel column purification were performed, thereby obtaining 2-fluoro-1-iodododec-1-ene and 2,2-difluoro-1,1-diiodododecane in a yield of 16% and a yield of 26%, respectively, as target products.

The invention claimed is:

1. A method for producing a fluorine and iodine adduct of a compound represented by formula (1):

wherein
R¹ and R² are each independently a hydrogen atom, a halogen atom, or an organic group, or R¹ and R² optionally form a ring together with the two adjacent carbon atoms;
n is 1 or 2; and
the symbol ≡ is a double bond or a triple bond,
with the proviso that
when the symbol is a triple bond, n is 1,
when the symbol is a double bond, n is 2,
two R¹s are optionally the same or different,
two R²s are optionally the same or different, or
two R¹s or two R²s optionally form a ring together with their adjacent carbon atom, the method comprising reacting the compound represented by formula (1) with
(A) at least one fluorine source selected from the group consisting of hydrogen fluoride, hydrogen fluoride salts, and fluoride salts,
(B) at least one iodine source selected from the group consisting of iodine and iodide salts, and
(C) at least one compound selected from the group consisting of oxidizing agents and radical generators,
to add fluorine and iodine to the double bond or triple bond,
wherein the compound (C) is at least one member selected from the group consisting of peroxides and metal oxides,
the peroxide is at least one member selected from the group consisting of hydrogen peroxide; perboric acid, percarbonic acid, perphosphoric acid, persulfuric acid, permanganic acid, and salts thereof; compounds represented by formula: $R^aCOOOM$, wherein $R^a$ is a hydrocarbon group optionally having one or more substituents, and M is a hydrogen atom or a metal atom;
compounds represented by formula: $R^bOOM$, wherein $R^b$ is a hydrocarbon group optionally having one or more substituents, and M is a hydrogen atom or a metal atom;
compounds represented by formula: $R^{c1}OOR^{c2}$, wherein $R^{c1}$ and $R^{c2}$ are each independently a hydrocarbon group optionally having one or more substituents or $R^{c3}$—CO—, and $R^{c3}$ is a hydrocarbon group optionally having one or more substituents; and
compounds represented by formula:

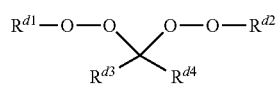

wherein $R^{d1}$ to $R^{d4}$ are each independently a hydrocarbon group optionally having one or more substituents, and $R^{d3}$ and $R^{d4}$ optionally form a ring together with the adjacent carbon atom,
the metal oxide is at least one selected from the group consisting of chromic acid, dichromic acid, tungsten oxide, ruthenium oxide, antimony oxide, and osmium oxide; and
wherein the temperature of the reaction is within the range of 0 to 40° C.

2. The production method according to claim 1, wherein the fluorine source is at least one member selected from the group consisting of hydrogen fluoride, hydrogen fluoride amine salts, and alkali metal fluoride salts.

3. The production method according to claim 1, wherein the amount of the fluorine source is within the range of 0.1 to 1000 moles, per mole of the compound represented by formula (1).

4. The production method according to claim 1, wherein the iodine source is at least one member selected from the group consisting of iodine and alkali metal iodide salts.

5. The production method according to claim 1, wherein the amount of the iodine source is within the range of 0.1 to 10 moles, per mole of the compound represented by formula (1).

6. The production method according to claim 1, wherein the compound (C) is a peroxide.

7. The production method according to claim 1, wherein the compound (C) is at least one member selected from the group consisting of hydrogen peroxide, peracetic acid, perbenzoic acid, metachloroperbenzoic acid, tert-butyl hydroperoxide, cumene hydroperoxide, sodium perborate, potassium persulfate, a potassium hydrogen persulfate-potassium hydrogen sulfate-potassium sulfate mixture, permanganic acid, dichromic acid, tungsten oxide, ruthenium oxide, antimony oxide, and osmium oxide.

8. The production method according to claim 1, wherein the amount of the compound (C) is within the range of 0.1 to 10 moles, per mole of the compound represented by formula (1).

9. The production method according to claim 1, wherein the reaction is performed in the presence of a solvent.

10. The production method according to claim 9, wherein the solvent is at least one member selected from the group consisting of aliphatic hydrocarbons, aromatic hydrocarbons, halogenated hydrocarbons, ethers, esters, nitriles, and water.

11. The production method according to claim 9, wherein the solvent is at least one member selected from the group consisting of aliphatic hydrocarbons, halogenated hydrocarbons, ethers, and water.

12. The production method according to claim 1, wherein the reaction is performed in the absence of $IF_5$.

13. The production method according to claim 1, wherein the reaction is performed at room temperature for 1 to 36 hours.

14. The production method according to claim 1, wherein $R^1$ and $R^2$ are each independently a hydrogen atom, a halogen atom, an alkyl group optionally having one or more substituents, an alkoxy group optionally having one or more substituents, a carboxyl group optionally having one or more substituents, a cycloalkyl group optionally having one or more substituents, an aryl group optionally having one or more substituents, or an aralkyl group optionally having one or more substituents, or $R^1$ and $R^2$ optionally form a ring together with the two adjacent carbon atoms.

15. The production method according to claim 14, wherein the one or more substituents in the alkyl, alkoxy, cycloalkyl, aryl, or aralkyl group are at least one member selected from the group consisting of halo, hydroxyl, alkoxy, carboxyl, alkylcarbonyl, alkylcarbonyloxy, and alkoxycarbonyl groups, and the one or more substituents in the carboxyl group are at least one member selected from the group consisting of halo and alkyl groups.

16. The production method according to claim 1, wherein the temperature of the reaction is within the range of 10 to 40° C.

* * * * *